US009536571B2

(12) United States Patent
Sutton et al.

(10) Patent No.: US 9,536,571 B2
(45) Date of Patent: Jan. 3, 2017

(54) DEBRIS REDUCING DISK CLAMP FOR DISK DRIVES

(71) Applicant: INTRI-PLEX TECHNOLOGIES, INC., Santa Barbara, CA (US)

(72) Inventors: Adam D. Sutton, Pleasanton, CA (US); David M. Erlach, Santa Barbara, CA (US); Frederic C. Petersen, Santa Barbara, CA (US); Ryan J. Schmidt, Santa Barbara, CA (US); Paul W. Smith, Santa Barbara, CA (US); Robert J. Tench, Goleta, CA (US)

(73) Assignee: INTRI-PLEX TECHNOLOGIES, INC., Santa Barbara, CA (US)

( * ) Notice: Subject to any disclaimer, the term of this patent is extended or adjusted under 35 U.S.C. 154(b) by 0 days.

(21) Appl. No.: 15/146,620

(22) Filed: May 4, 2016

(65) Prior Publication Data
US 2016/0247546 A1    Aug. 25, 2016

Related U.S. Application Data

(62) Division of application No. 14/165,164, filed on Jan. 27, 2014, now Pat. No. 9,361,929, which is a division
(Continued)

(51) Int. Cl.
| | |
|---|---|
| *G11B 17/022* | (2006.01) |
| *G11B 33/14* | (2006.01) |
| *C12N 15/82* | (2006.01) |
| *G11B 17/028* | (2006.01) |
| *G11B 17/038* | (2006.01) |

(52) U.S. Cl.
CPC ....... *G11B 33/1446* (2013.01); *C12N 15/8233* (2013.01); *C12N 15/8281* (2013.01); *C12N 15/8286* (2013.01); *C12N 15/8289* (2013.01); *G11B 17/022* (2013.01);
(Continued)

(58) Field of Classification Search
None
See application file for complete search history.

(56) References Cited

U.S. PATENT DOCUMENTS

| | | |
|---|---|---|
| 5,392,178 A | 2/1995 | Nishio et al. |
| 5,517,374 A | 5/1996 | Katakura et al. |
| | (Continued) | |

FOREIGN PATENT DOCUMENTS

| | | |
|---|---|---|
| JP | 2008077807 | 4/2008 |
| JP | 2009076117 | 4/2009 |

*Primary Examiner* — Will J Klimowicz (57) ABSTRACT

A disk clamp for clamping a plurality of disks within a disk drive has a single fastening hole located at its symmetrical center sized to pass the shaft of a screw having a head diameter larger than the fastening hole. The screw fastens the disk clamp to a motor hub supporting the plurality of disks. The disk clamp has a moat around the fastening hole, at a maximum diameter that is smaller than the head diameter of the head on the fastening screw. The moat may be circular, have spike trenches angled toward the fastening hole, or be spiral. The diameter of the spiral moat decreases in a clockwise or counterclockwise direction toward the fastening hole. The midsection of the disk which the screw head covers is biased at a negative angle toward the fastening hole forcing particles generated during assembly toward the fastening hole of the disk clamp.

11 Claims, 8 Drawing Sheets

Related U.S. Application Data of application No. 13/445,726, filed on Apr. 12, 2012, now Pat. No. 8,675,306.

(52) U.S. Cl.
CPC ...... *G11B 17/0284* (2013.01); *G11B 17/0287* (2013.01); *G11B 17/038* (2013.01)

(56) References Cited

U.S. PATENT DOCUMENTS

| | | |
|---|---|---|
| 5,528,434 A | 6/1996 | Bronshvatch et al. |
| 5,615,067 A | 3/1997 | Jabbari et al. |
| 5,668,427 A | 9/1997 | Morita |
| 5,912,784 A | 6/1999 | Bronshvatch et al. |
| 5,943,184 A | 8/1999 | Kelsic et al. |
| 6,462,903 B1 | 10/2002 | Yamada et al. |
| 6,483,661 B1 * | 11/2002 | Martin ................ G11B 17/038 360/98.08 |
| 6,703,584 B2 | 3/2004 | Church et al. |
| 6,822,826 B2 | 11/2004 | Choo et al. |
| 7,027,261 B2 | 4/2006 | Momoi |
| 7,209,320 B1 | 4/2007 | Woods et al. |
| 7,215,509 B2 | 5/2007 | Ng |
| 7,826,173 B2 | 11/2010 | Lee |
| 8,321,884 B2 | 11/2012 | Suzuki |
| 8,675,306 B2 | 3/2014 | Sutton et al. |
| 2005/0099723 A1 | 5/2005 | Momoi |
| 2010/0265615 A1 * | 10/2010 | Yamaguchi ........ G11B 17/0284 360/99.12 |

\* cited by examiner

DEBRIS REDUCING DISK CLAMP FOR DISK DRIVES

CROSS REFERENCE TO RELATED APPLICATIONS

This application is a divisional of application Ser. No. 14/165,164 filed Jan. 27, 2014 for Debris Reducing Disk Clamp for Disk Drives, which is a divisional of application Ser. No. 13/445,726 filed Apr. 12, 2012, now U.S. Pat. No. 8,675,306, granted Mar. 18, 2014 for Debris Reducing Disk Clamp For Disk Drives.

BACKGROUND OF THE INVENTION

1. Field of the Invention

The present invention relates to disk drives and more specifically, to a disk clamp for a disk drive that reduces debris migration onto the disk surface.

2. Description of Related Art

Work stations, personal computers and laptop computers require disk drives that provide a large amount of data storage within a minimal physical area. A disk drive typically includes one or more hard disks that are rotated at a constant high speed by a spindle motor. Generally, disk drives operate by positioning a transducer or read/write head over respective tracks on the disks. The information is written to and read from tracks on the disks through the use of an actuator assembly which rotates during a seek operation. The actuator is coupled to control electronics which control the positioning of the actuator and the read/write functions of the transducer. A typical actuator assembly includes a plurality of actuator arms which extend towards the disks with one or more flexures extending from each of the actuator arms. Mounted at the distal ends of each of the flexures is a head which acts as an air bearing enabling the head to fly in close proximity above the corresponding surface of the associated disk. The demand for increasing density of information stored on these disks is becoming greater and greater for a multitude of reasons. The increase of multi-user and multi-tasking operating system work stations which provide an operating environment requiring the transfer of large amounts of data to or from the hard disks, large application programs, the popularity of notebook and laptop computers and the continuing trend toward higher performance microprocessors all contribute to this end. The structural designs of these systems are also continually shrinking, requiring hard disk drives having high capacity storage capability while occupying a minimal amount of space within the system.

In order to accommodate these demands, there is a need for smaller hard disk drives which have increased storage capacity. To read this more densely stored information, engineers have decreased the gap fly height between the heads and the disks. Reducing the gap fly height leads to increased contact between a head and the data portion of the disk during operation of the disk drive. Nevertheless, there has been an industry wide push to reduce the height at which transducers are maintained over the disk surface without actually contacting the disk surface.

When a transducer flies over a rotating disk, the flying height tends to fluctuate slightly above and below a normal flying height because the disk surface itself is not flat. At lower flying heights the variation in the fly height may cause the transducer to contact the disk surface. This intermittent contact, if repeated, can damage the transducer or the disk and may cause drive failures.

In conventional disk drives, a stack of disks is provided on a cylindrical hub of a spindle motor. A disk clamp is provided on top of the stack of disks on the hub. The clamp has a larger radius than that of the hub so that the outer diameter of the clamp is in contact with the top disk. A plurality of screws, or a single screw, fit through holes located in the disk clamp. These screws (screw) are threaded into bores in the hub. When a screw is tightened, the force applied to the midsection of the disk clamp is transferred to the outer circumference of the disk clamp which contacts the disk surface. This force secures the disks to the spindle motor hub. The disks must be secured under considerable force in order to prevent any slippage of one or more disks in the presence of mechanical shocks. Even very slight slippage of a disk within a drive could result in mechanical misalignment of the transducer which could result in data transfer errors or failure.

The assembly of the disk clamp over the disk stack tends to generate minute particles which tend to disburse on the surface of the disks themselves. These small particles contribute to transducer contact with the disk surface, culminating in head crashes. The more fastening screws utilized to secure the disk clamp to the spindle motor, the more opportunity there is for the generation of these minute particles.

Accordingly, there is a need for a disk clamp that prevents dispersal of particles generated during assembly of the disk stack. The present invention provides a solution to this problem.

SUMMARY OF THE INVENTION

The generation of debris particles during assembly of a disk pack in a disk drive is considerably ameliorated by trapping these particles in a moat formed into the disk clamp surrounding the fastening hole. The moat is covered by the head of the screw fastening the disk clamp to the motor hub. The moat keeps the debris generated during torque-down of the screw on the inside of the moat, between the moat and fastening hole. Various moat designs have been found to be effective. Besides a circular moat, a spike trench moat having trenches angled toward the fastening hole, or a spiral moat are effective in retaining debris under the head of the screw. Another preferred method of retaining debris under the head of the fastening screw biases the area surrounding the fastening hole (the midsection) at to a negative angle towards the fastening hole of the disk clamp. This negative angle of the midsection forces particles generated during assembly inward, toward the fastening hole, trapping the particles under the head of the fastening screw.

BRIEF DESCRIPTION OF THE DRAWINGS

The exact nature of this invention, as well as the objects and advantages thereof, will become readily apparent from consideration of the following specification, in conjunction with the accompanying drawings, in which like reference numerals designate like parts throughout the figures thereof and wherein.

DETAILED DESCRIPTION OF THE PREFERRED EMBODIMENTS

Figure 1:
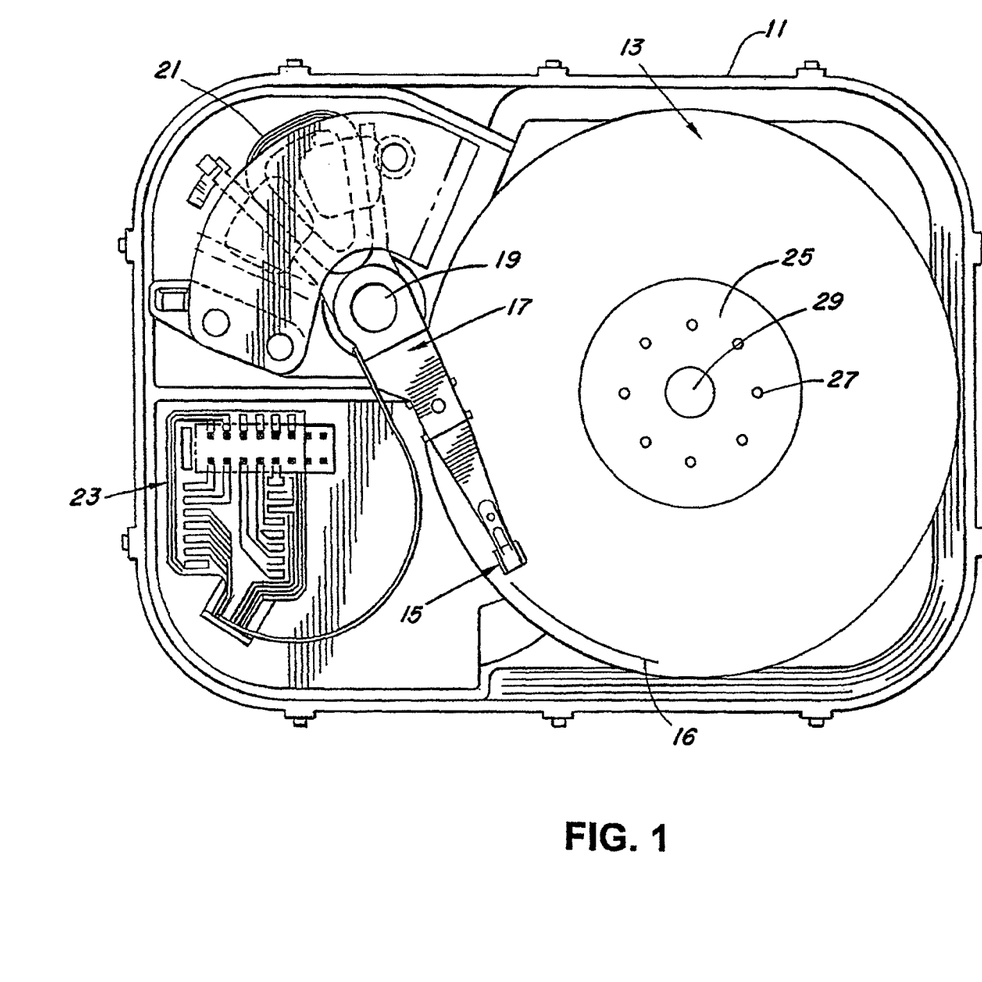
FIG. 1 shows a top cut-away view of an assembly of a disk drive.

FIG. 1 represents a cut-away top view of a disk drive 11 having one or more hard disks 13 with each of the hard disks having information written in a series of data tracks 16 thereon. The disk drive 11 utilizes at least one transducer 15 for reading and writing information to the hard disk 13. The transducer 15 may be a conventional conductive element or may be a magneto-resistive element, for example. The transducer 15 is connected to an actuator arm 17. The movements of the actuator arm 17 are controlled by a voice coil motor 21 to pivot about a pivot junction 19. A control circuitry 23 is used to control the operation of the actuator arm 17 and other components (not shown) within the disk drive 11.

During a seek operation, for example, the track position of the head 15 is moved across the surface of the disk 13. The head 15 is connected to the actuator arm 17 by a flexure 51.

The hard disk 13 may be a single disk or a stack of disks. The hard disk 13 is connected to a spindle motor (not shown) by a disk clamp 25. According to the present invention, the disk clamp attaches the hard disk 13 to the hub of the spindle motor by a screw 29. A plurality of holes 27 are located in the disk clamp 25 circumferentially spaced about the fastening screw 29.

The disk clamp 25 affixes the hard disk 13 to the hub of the motor by the force exerted by the fastening screw 29. During operation of the disk drive 11, the hard disk 13 is rotated by the motor, and the actuator arm 17 moves the transducer 15 across the surface of the hard disk 13 transferring data between the transducer 15 and the hard disk 13.

Figure 2:
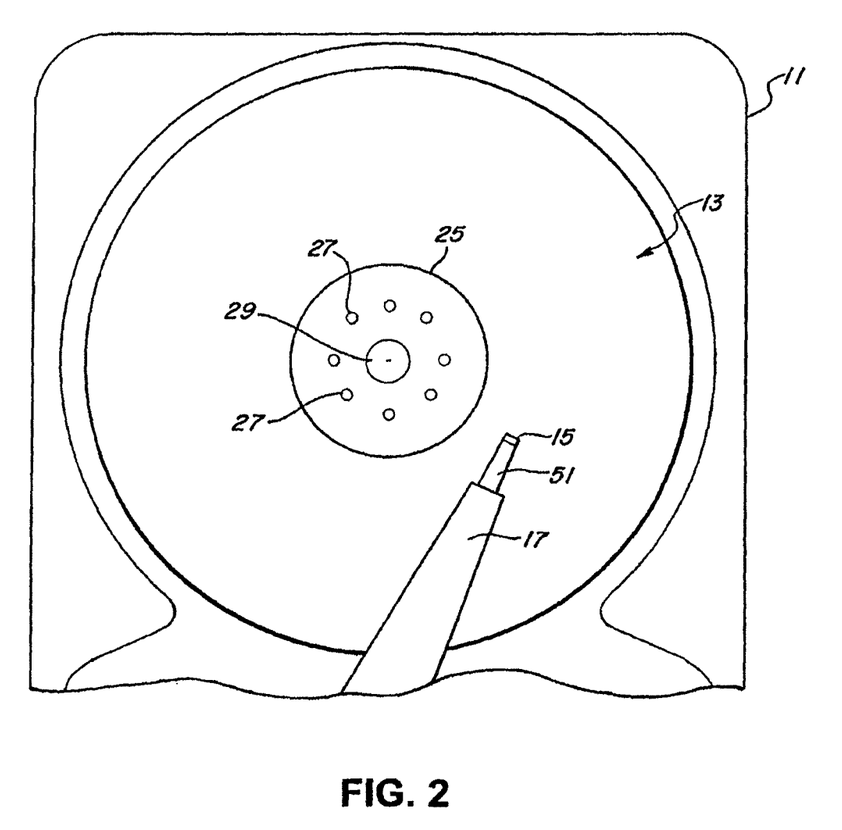
FIG. 2 shows a top cut-away view of the disk stack in a disk drive.
Figure 3:
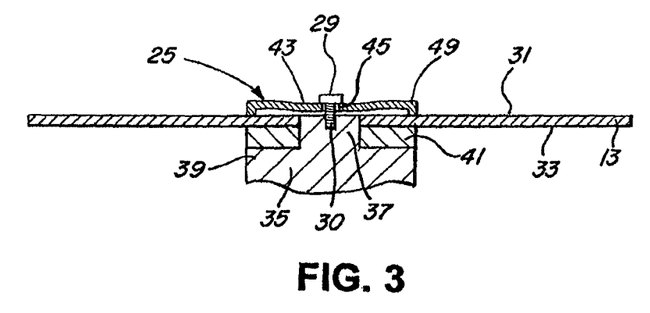
FIG. 3 is a cross-section of the disk clamp and drive motor hub assembly.
Figure 4:
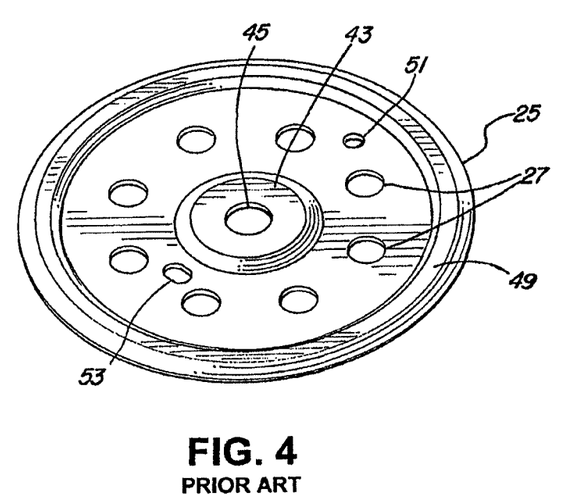
FIG. 4 is a perspective of a prior art disk clamp.

Referring to FIGS. 2, 3 and 4, a spindle motor (not shown) carries the generally cylindrical hub 35 which has a cylindrical bottom flange 39 and a cylindrical head 37 extending upward from the flange 39. The head 37 defines a centrally located fastener bore 30. The flange 39, hub 35, head 37 and fastener bore 30 are all preferably substantially concentric. It should be noted, however, that the hub may have many different configurations in accordance with the present invention. For example, the hub can include several circumferentially spaced fastener bores rather than a single centrally located fastener bore 30. The disk pack assembly illustrated for the disk 13 includes an annular spacer 41 that is seated on the hub 35 so that it extends around the head 37 and rests on the flange 39. It should be kept in mind that the present invention can be used without the spacer 41. Also in an embodiment where the disk drive includes multiple disks 13, a plurality of spacers 41 are used to separate each of the disks 13. The disk 13 is in turn seated on the hub 35 so that it extends about the hub head 37 and rests on the spacer 41. The disk 13 has a lower data surface 33 and an upper data surface 31.

The disk pack assembly shown in FIG. 3 includes a disk clamp 25. Disk clamp 25 is shown separately in FIG. 4. Disk clamp 25 is centrally located on the upper surface 31 of the disk 13. A rim 49 forms the periphery or outer diameter of the disk clamp 25. A concentrically located fastening hole 45 in the disk clamp defines a centrally located space for insertion of a fastening screw 29.

It should be kept in mind that multiple circumferentially spaced fastener holes 45 may be utilized to match up with multiple fastener bores 30 in the hub head 37. The disk clamp 25 is preferably made of stainless steel, although it could be made of aluminum or materials or alloys having similar desired characteristics.

Fastening screw 29 extends through the fastener hole 45 of the disk clamp 25 and into the fastener bore 30 in the hub 35. The fastening screw 29 engages the hub 35 and draws the central midsection 43 of the disk clamp 25 downward beyond its normal resting position, thereby creating stress and a constant downward pressure at the rim 49. The rim 49 in turn applies a downward pressure on the upper surface 31 of disk 13, thereby holding the disk 13 securely in place on the hub 35.

FIG. 4 illustrates a prior art disk clamp 25. A fastening hole 45 is centrally located within the disk clamp 25 which is preferably formed as a circular member. A plurality of through holes 27 are circumferentially located about the centrally located fastening hole 45 in the main portion of the disk clamp 25. A midsection 43 surrounds the fastening hole 45 inside the balance holes 27. Tooling holes 51, 53 are located in the body of the disk clamp between the midsection and outer diameter of the disk clamp. These holes may be utilized by a spanner type tool that is inserted during assembly to keep the disk clamp and spindle motor from turning as the screw attaching the disk clamp 25 is tightened. These holes are also utilized as a reference marker for locating a reference for placing weights in the weight holes 27, to balance the disk pack after assembly.

Figure 5:
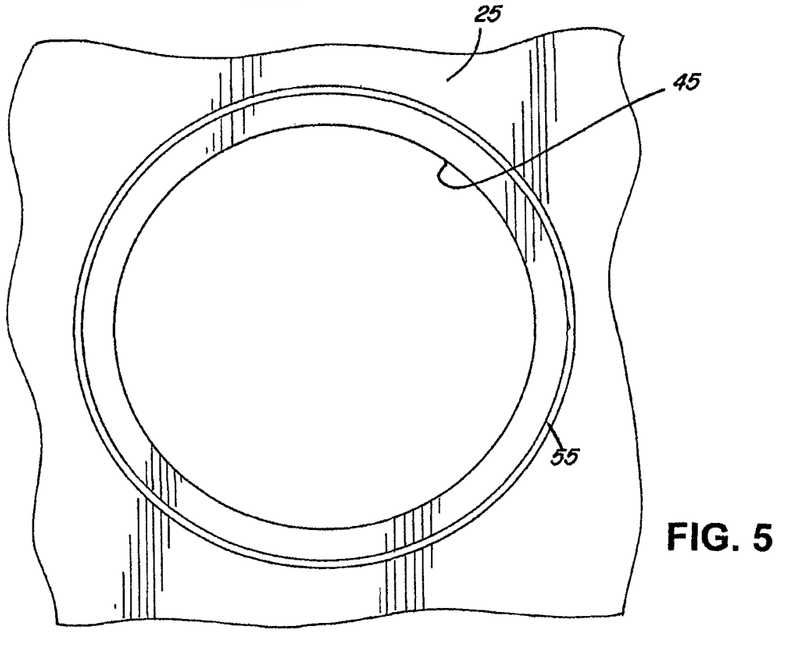
FIG. 5 is a top view of a disk clamp at the fastening hole, illustrating one embodiment of the invention.

FIG. 5 is a top view of a disk clamp according to a preferred embodiment of the present invention. FIG. 5 shows the midsection area of the disk clamp 25. Surrounding the fastening hole 45 is a moat 55 that may be etched, laser cut, or metal worked (coined) into the disk clamp.

Figure 6:
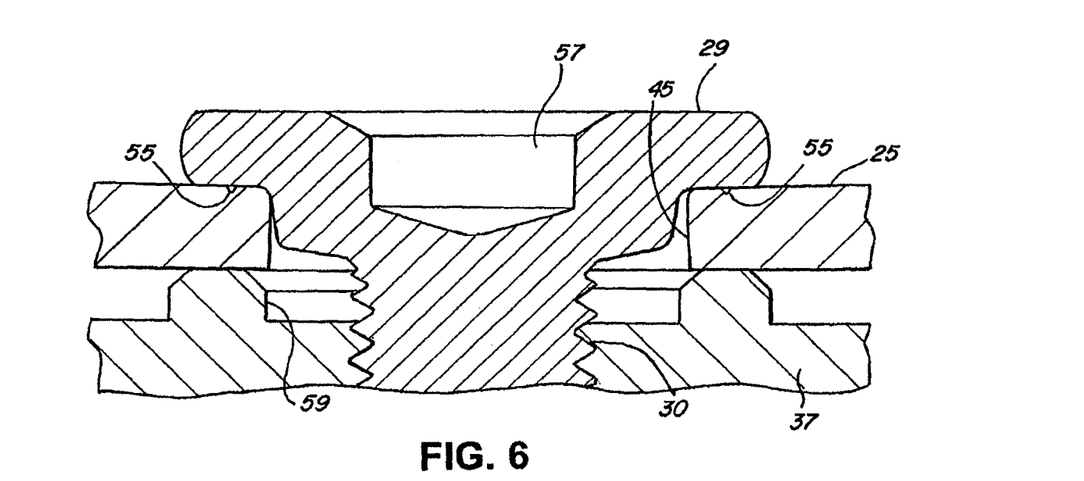
FIG. 6 is a cross-section of the disk clamp at the fastening hole attached to the motor hub by a fastening screw.

FIG. 6 is a cross-sectional view of the disk clamp 25 of FIG. 5 being held to the head 37 of the hub 39 (not shown). The fastening screw 29 has an internal fastening slot 57 which may be hexagonal, for example. The head on screw 29 overlaps the edges of the disk clamp 25 at the fastening hole 45. Circumferentially located around the fastening hole 45 is the moat 55. The moat 55 is located underneath the head of fastening screw 29 when the disk clamp is being held down by the screw 29.

Figure 7:
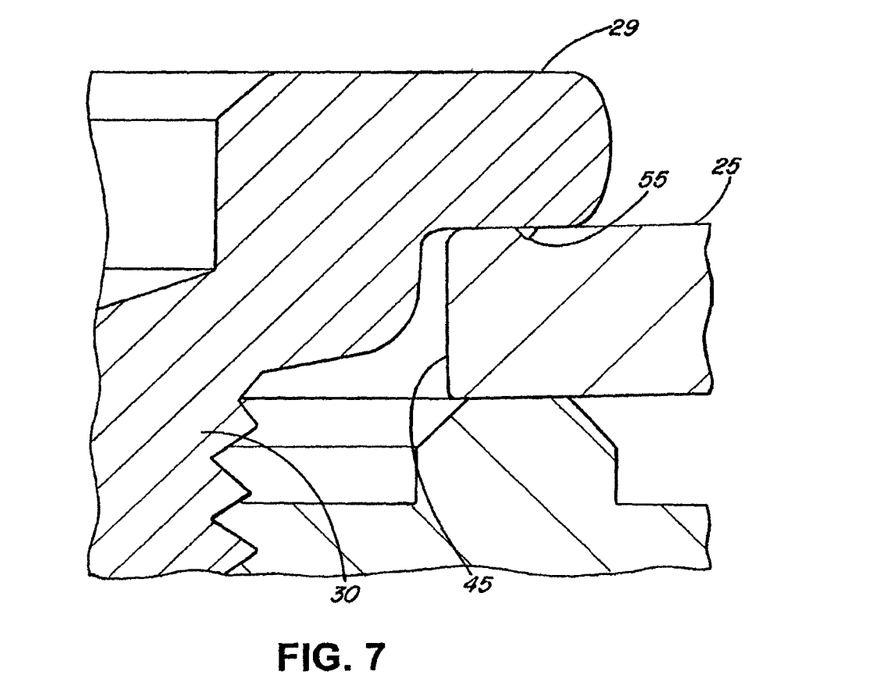
FIG. 7 is a cross-section expanded view of one side of the fastening screw holding down the disk clamp.

FIG. 7 illustrates more clearly the moat 55 located under the head of fastening screw 29 when the screw 29 is threaded into the hub 37.

The moat 55 has a width measured at its mouth and a depth measured from the surface of disk clamp 25 to the deepest part of the moat. The moat preferably ranges in depth from 0.00068 inches to 0.00184 inches. The moat preferably varies in width from 0.00200 inches to 0.00427 inches.

The size of the moat must not be so large that it structurally impairs the disk clamp at this fastening point. Yet, the moat should be large enough to perform its function of maintaining debris formed as a result of tightening the screw 29 down over the surface of the disk clamp 25 in the area of the fastening hole 45 between the fastening hole and the moat trapped under the head of the bolt 29.

Considerable experimentation by the inventors with the disk clamp utilizing the moat as described above, surprisingly revealed that debris within the disk drive on the surface of the hard disks was reduced while debris between the moat 55 and the edge of the disk clamp hole 45 was increased.

Figure 8:
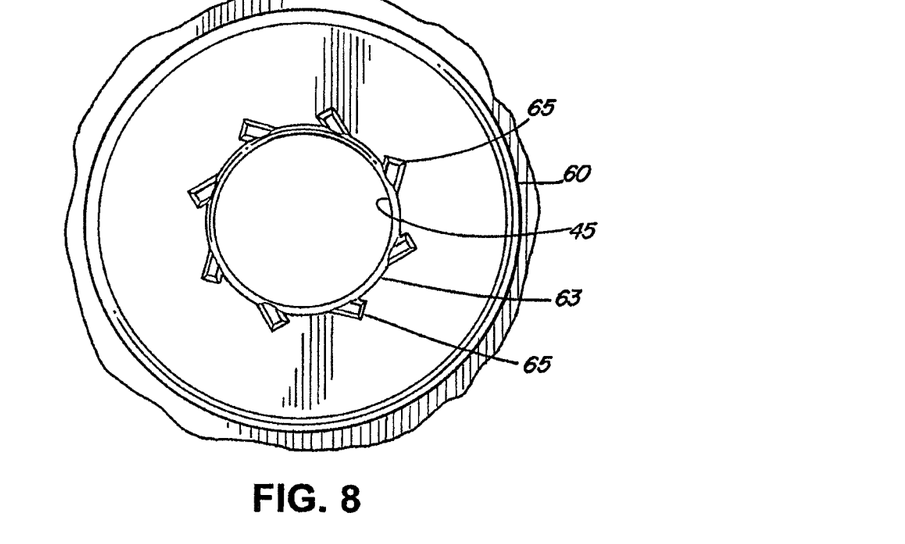
FIG. 8 is a top view illustration of a disk clamp according to another preferred embodiment.
Figure 9:
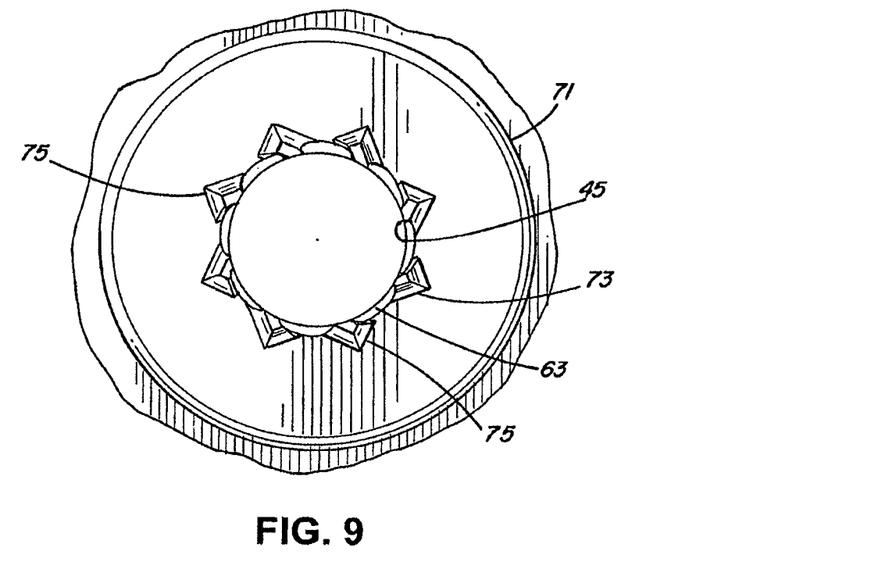
FIG. 9 is a top view illustration of a disk clamp according to yet another preferred embodiment.

FIGS. 8 and 9 illustrate alternative embodiments of the moat described above. Rather than a continuous moat circumferentially surrounding a fastening hole, a plurality of trenches 65, 75 angled towards the center of the fastening hole surround the fastening hole 45. Each of the trenches 65 are angled towards the center of the fastening hole so that particles that are being generated by tightening of the screw onto the disk clamp 60 are moved inward and fall into one of the multiple moats 65. The angle at which the trenches 65, 75 are placed may vary. The trenches may be curved in a clockwise direction or counterclockwise direction, depending on the threading direction of the screw so that the tightening of the screw is in a direction that moves particles being generated into the trenches 65, 75.

FIG. 9 shows a disk clamp 71 wherein the trenches 75 have smooth tops 73. These smooth tops eliminate scraping on the bottom of the screw head, thereby reducing the number of particles generated. The number of trenches 65, 75 used in the embodiments shown in FIGS. 8 and 9 preferably vary between 4 to 12, depending on the material used for the disk clamp and the tightening force required. The depth and width of the trenches 65, 75 of FIGS. 8 and 9 are comparable in size to the circumferential trench 55 shown in FIGS. 5 and 6.

Figure 10:
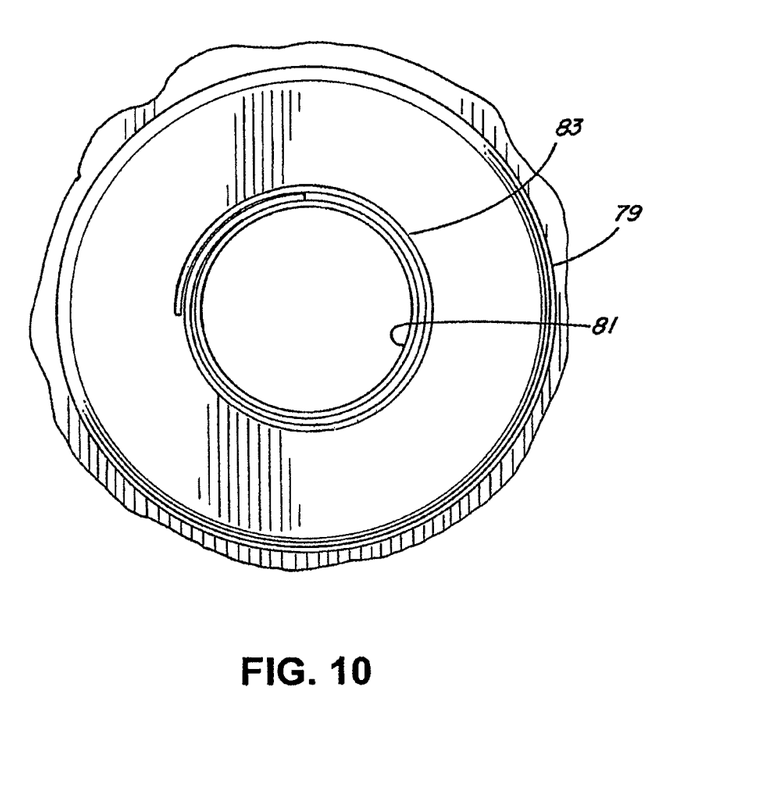
FIG. 10 is a top view illustration of yet another preferred embodiment.

Referring now to FIG. 10, a disk clamp 79 is shown having a fastening hole 81 with a spiral moat 83 surrounding the fastening hole 81. The spiral moat does not have a constant radial distance from center, as does the circumferential moat of FIG. 5. Rather, it decreases to the center, in a clockwise or counterclockwise direction, depending on the direction the fastening screw threads to tighten down the disk clamp.

The diameter of the outermost portion of the spiral moat, the spike trenches, and the circumferential moat, described above, is always less than the head diameter of the fastening screw.

Figure 11:
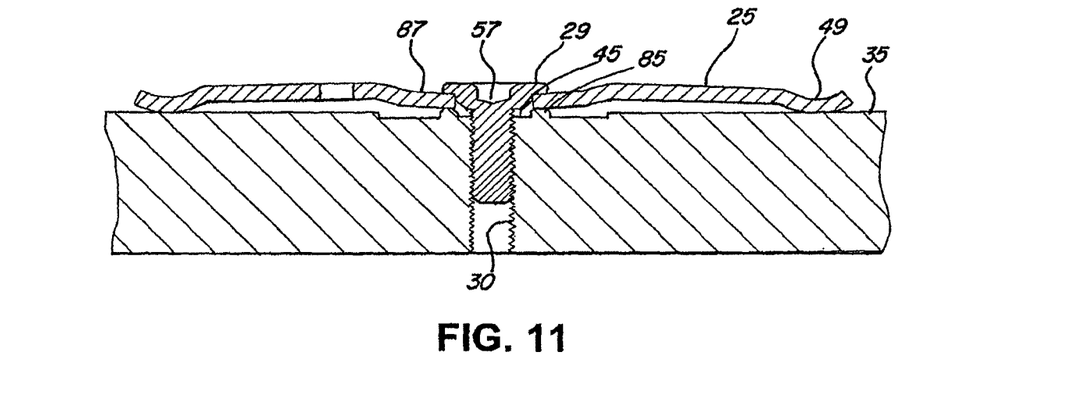
FIG. 11 is a cross-section of a disk clamp attached to a spindle motor hub by a single screw.
Figure 12:
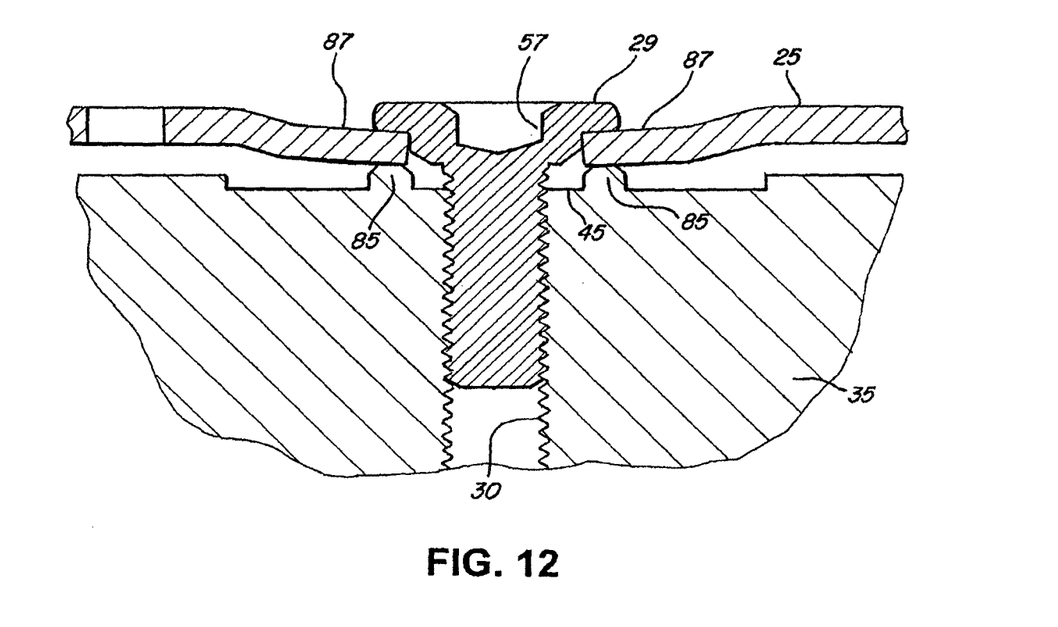
FIG. 12 is a cross-section expanded view of a disk clamp attached to a motor hub by a single screw showing an alternate preferred embodiment of the disk clamp.
Figure 13:
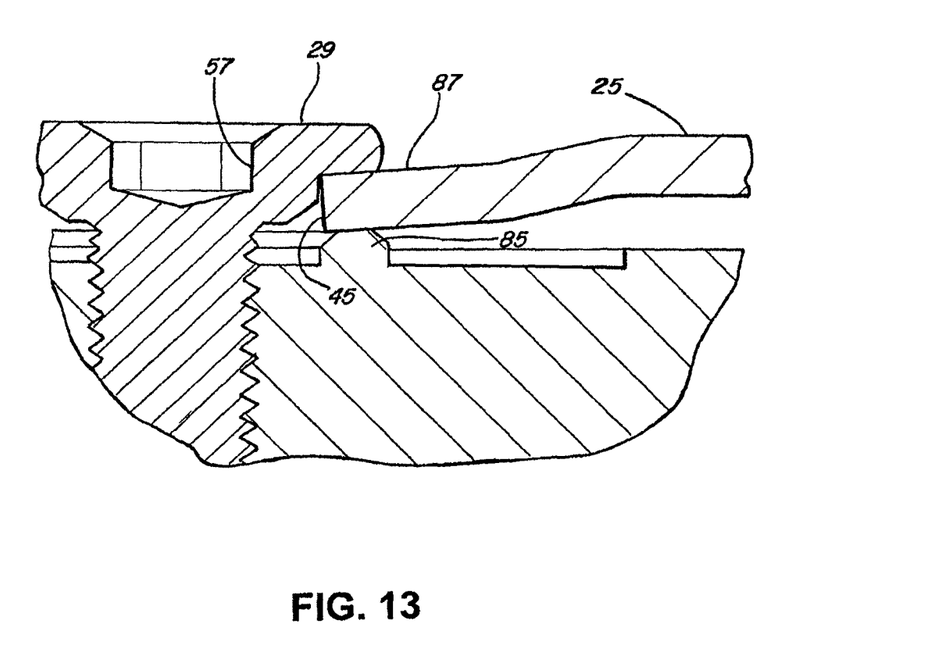
FIG. 13 is a cross-section expanded view of a disk clamp of FIG. 12 being attached to a motor hub by a single screw showing the contact area between the screw head and the disk clamp.

FIGS. 11, 12 and 13 illustrate an alternate embodiment of the present invention which is also designed to maintain particles generated during assembly trapped under the head of the fastening screw 29. As shown in FIG. 11, a disk clamp 25 having a fastening hole 45 within which is located a fastening screw 29 that threads into the hub 35 by way of a fastener bore 30 in hub 35. The disk clamp 25 has a midsection 87 surrounding the fastening hole 45.

Standard practice in the prior art is to bias this midsection 87 so that when the head of the fastening screw 29 compresses the midsection 87 of the disk clamp to the hub 35, the midsection 87 will flatten.

Offset angles are also used in other parts of a disk clamp. As taught in U.S. Pat. No. 7,209,320, the outside diameter of the disk clamp, at the disk to hub contact area has an offset angle that slopes downward from an inside to outside of the disk clamp contact point. The application of pressure during clamping will thus provide a more flat uniform contact area along the clamp surface. The prior art does not contemplate biasing the midsection of the disk clamp as proposed by the present invention or even recognize the reasons for doing so.

Contrary to this general wisdom, the present invention biases the midsection 87 around fastening hole 45 of the disk clamp 25 in a negative downward direction between 0 and −3.5 degrees. This negative angle is more clearly shown in FIGS. 12 and 13. The midsection 87 of the clamping disk 25 is angled downward when it is fastened by the head of the fastening screw 29. By biasing the midsection downward in this manner, the particles generated during threading of the screw 29 into the hub 35 are forced inward, towards the fastening hole 45. The inventors believe that the negative angle contributes to this movement of particles. Initial contact between the head of fastening screw 29 and the midsection 87 of the disk clamp is at the outside diameter of the screw head, cutting off any movement of particles past this initial contact point.

Experimentation by the inventors has found that considerably more particles are trapped under the head of the fastening screw 29 when the midsection 87 of the disk clamp is biased at a negative angle than as compared to a disk clamp that is biased positively in an upward direction, or a disk clamp that is flat.

It should be understood that the foregoing disclosure describes only the preferred embodiments of the invention. Various modifications may be made therein without departing from the spirit and scope of the invention as set forth in the claims to provide a disk clamp that traps debris particles generated during assembly of the disk pack in a disk drive. The particles are trapped underneath the head of the fastening screw.

What is claimed is:

1. A disk clamp for a disk drive, the disk drive including at least one storage disk supported on a hub rotated by a motor, the disk clamp comprising:
   a circular member having a center, a top surface and a bottom surface and an outer diameter, at least one fastening hole centrally located in the circular member sized for passing a shaft of a fastening screw that threads into the hub, the fastening screw having a head diameter larger than the shaft diameter, a moat having a plurality of spike trenches surrounding the fastening hole, each trench angled toward the fastening hole, formed into the circular member around the fastening hole, the moat having a diameter larger than the fastening hole but smaller than the head diameter of the fastening screw.

2. The disk clamp of claim 1 wherein the spiked trenches are straight.

3. The disk clamp of claim 1 wherein the spiked trenches are curved in a clockwise or counterclockwise direction, depending on the thread direction of the fastening screw.

4. The disk clamp of claim 1 wherein the top of the trenches are smooth.

5. The disk clamp of claim 1 wherein the spiked trenches are about 0.00068 inches to 0.00184 inches in depth.

6. The disk clamp of claim 1 wherein the spiked trenches are about 0.00200 inches to 0.00427 inches wide.

7. The disk clamp of claim 1 wherein 4 to 12 spike trenches surround the fastening hole.

8. A disk clamp for a disk drive, the disk drive including at least one storage disk supported on a hub rotated by a motor, the disk clamp comprising:

a circular member having a center, a top surface and a bottom surface and an outer diameter, at least one fastening hole centrally located in the circular member sized for passing a shaft of a fastening screw that threads into the hub, the fastening screw having a head diameter larger than the shaft diameter, a moat spiraling with a decreasing diameter toward the fastening hole in a clockwise or counterclockwise direction formed into the circular member around the fastening hole, the moat having a diameter larger than the fastening hole but smaller than the head diameter of the fastening screw.

9. The disk clamp of claim 8 wherein the outside diameter of the moat is smaller than the head diameter of the fastening screw.

10. The disk clamp of claim 8 wherein the spiral moat has a depth of about 0.00068 inches to 0.00184 inches.

11. The disk clamp of claim 8 wherein the spiral moat has a width of about 0.0020 inches to 0.0047 inches.

* * * * *